United States Patent [19]

Franko

[11] Patent Number: 4,693,719
[45] Date of Patent: Sep. 15, 1987

[54] MECHANICAL PENILE PROSTHESIS

[75] Inventor: Zenon Z. Franko, Union, N.J.

[73] Assignee: C. R. Bard, Inc., Murray Hill, N.J.

[21] Appl. No.: 701,771

[22] Filed: Feb. 14, 1985

[51] Int. Cl.⁴ ............................. A61F 2/26; A61F 5/00
[52] U.S. Cl. .......................................... 623/11; 128/79
[58] Field of Search ................... 403/56, 90, 138, 144; 3/1, 36; 128/1 R, 79

[56] References Cited

U.S. PATENT DOCUMENTS

| 443,769 | 12/1890 | Hurford | 403/56 |
| 1,500,921 | 7/1924 | Bramson et al. | 403/56 |
| 1,639,441 | 8/1927 | Spahr | 403/90 |
| 2,456,182 | 12/1948 | Goble | 403/56 |
| 2,918,338 | 12/1959 | Grad | 403/56 |
| 4,151,840 | 5/1979 | Barrington | 128/79 |
| 4,343,360 | 10/1982 | Finney et al. | 128/79 |
| 4,411,261 | 11/1983 | Finney | 128/79 |

Primary Examiner—R. J. Apley
Assistant Examiner—David J. Isabella
Attorney, Agent, or Firm—Kane, Dalsimer, Kane, Sullivan and Kurucz

[57] ABSTRACT

Disclosed is a fully implanted mechanical penile erection device. Two or more cylindrical segments lock into an axially aligned position. The locking is accomplished by the action of a spring plunger pressing a flat rider against the surface of an adjacent segment or a dumbbell shaped connector.

12 Claims, 5 Drawing Figures

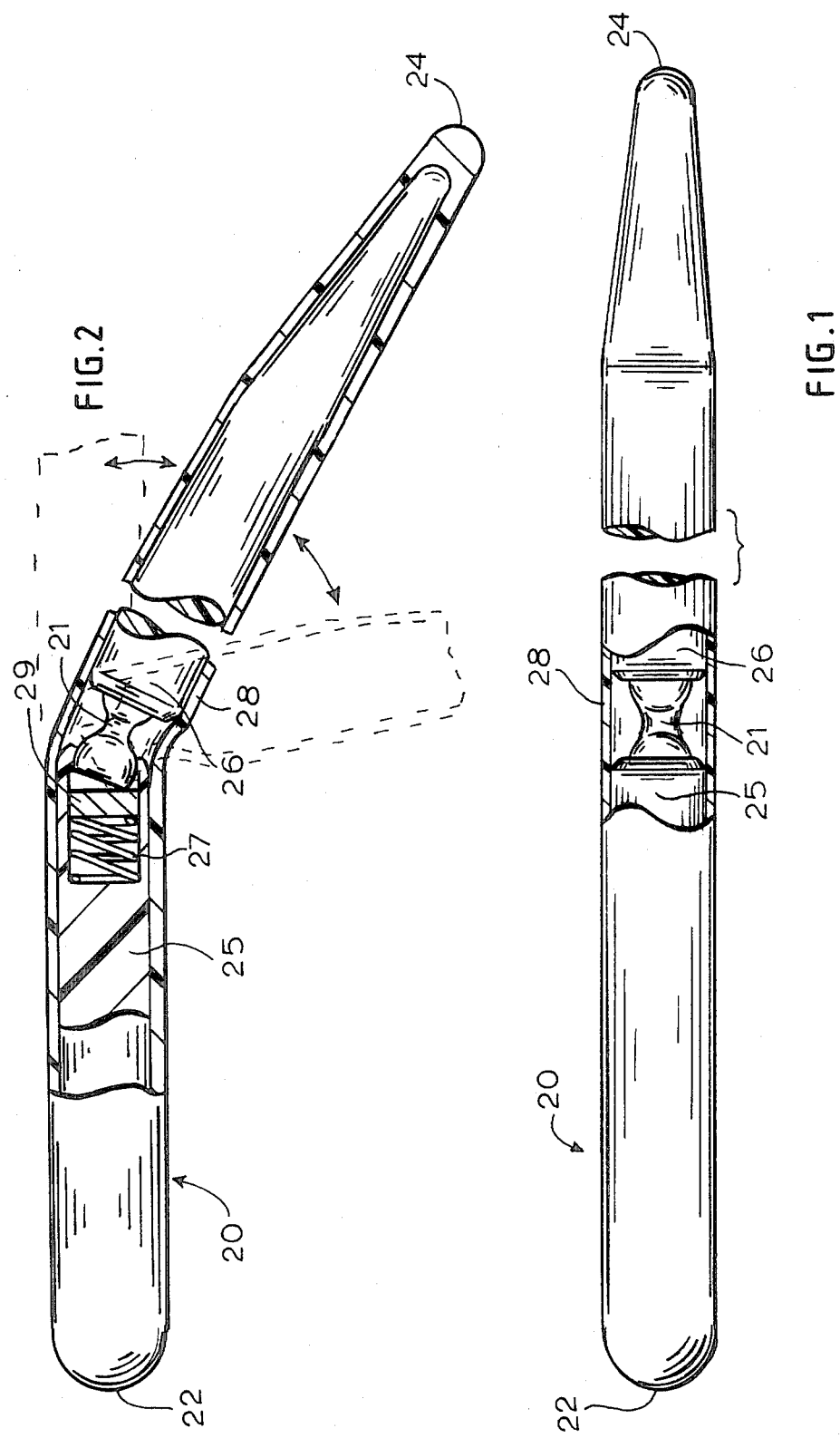

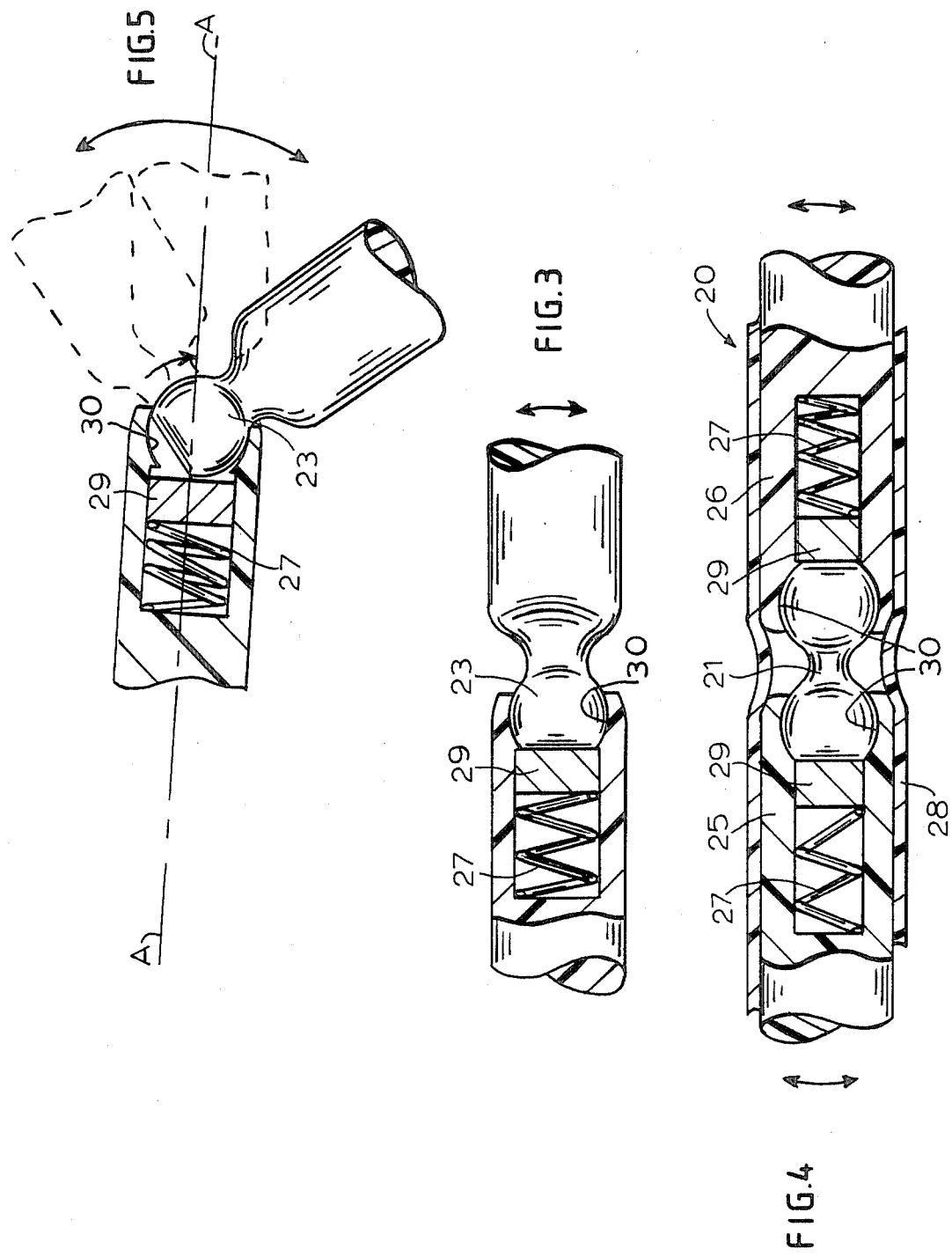

MECHANICAL PENILE PROSTHESIS

BACKGROUND OF THE INVENTION

This invention relates to a mechanical prosthesis which provides erections for human males who suffer the dysfunction of erectile impotence.

Various implantable devices for achieving penile erection have been developed. These devices are classified as either mechanical or the more recently developed inflatable devices. The inflatable devices involve an implantable hydraulic fluid transfer system where the corpora are inflated and deflated at will in an attempt to closely approximate the physiological state of the penis in its erect and flaccid states.

The inflatable prosthesis appear to have excellent potential; however, at present, they have shortcomings. For example, the pump and release valves are frequently located in the scrotum, which is one of the body's sites most disposed to post-operative discomfort and infection. Some inflatable devices require one or more minutes of pumping to inflate. Furthermore, extensive surgery is required and both hydraulic and mechanical failures have been experienced.

The mechanical prosthesis were originally stiff rods designed to be implanted in the corpora cavernosa to attain penile erection. Although this system provides a longer, thicker and stiffer erectile state, the flaccid state is no longer achievable—the patient has a permanent erection. Furthermore, fractures during intercourse have been experienced with the stiff rods. After fracture the penis is frail and no longer functional for intercourse.

Flexible rods have been developed to overcome the shortcomings of the stiffer rods. Timm in U.S. Pat. No. 3,987,789 describes a prosthesis including an elongated malleable rod portion housed within a generally tubular physiologically inert plastic body. The malleable rod portion enables the prosthesis to be conformed to a variety of shapes by bending or twisting. During intercourse the prosthesis will maintain the penis in a erectile state and afterwards the penis may be positioned and maintained by the user in a convenient, comfortable position. Flexible rods of this type have been successful, however the penis still does not feel physiologically normal. The penis does not bend freely as it naturally does in the flaccid state. Moreover, one of the most annoying problems of the malleable rod implant is its tendency to creep up, and, consequently must frequently be repositioned.

The latest concept in mechanical implants rods comprised of hinged segments or links. The hinged rods allow the penis to bend more freely.

Barrington in U.S. Pat. No. 4,151,840 describes a hinged mechanical penile prosthesis, which is comprised of a plurality of independent segments or links enclosed in a pre-stretched tubular sheath. The sheath maintains the segments in link-to-link contact, so that on straightening a concave end of a segment mates a convex end of an adjacent segment whereby the segments are aligned into a straight rod, resulting in an erect penis.

SUMMARY OF THE INVENTION

The present invention relates to hinged mechanical penile prosthesis designed to be surgically implanted in the penis for the treatment of erectile impotence or as a functional component of a penile replacement prosthesis.

The penile prosthesis of the present invention advantageously eliminates the tendency of the prosthesis to creep up as is the case with malleable rod implants. The prosthesis also provides for the patient to induce a penile erection at will.

The penile prosthesis, according to the invention, consists of at least two relatively rigid, cylindrically-shaped end segments. In one form of the invention a connector joins two adjacent segments. In another form the segments are designed to connect directly with each other. The invention relies on a locking mechanism which will cause the two adjacent segments to self-lock in an axially aligned or erect position. In the unlocked position the segments are still joined and pivotal or bending motion of the prosthesis is possible in all directions (360 degrees) about the longitudinal axis of the prosthesis.

In the preferred embodiment of the invention the segments are joined by a dumbbell-shaped connector mating in a ball socket of the segment. A spring plunger pressing a flat rider against a flat surface on the connector lock the segments in the erect position. A sheath surrounds the segments and connectors. A lubricant may be positioned inside the sheath if necessary to insure long life of the prothesis.

These and various other advantages and features of novelty which characterize the invention are pointed out with particularity in the claims annexed hereto and forming a part hereof. However, for a better understanding of the invention, its advantages, and objects attained by its use, reference should be had to the drawings which form a further part hereof, and to the accompanying descriptive matter, in which there is illustrated and described a preferred embodiment of the invention.

BRIEF DESCRIPTION OF THE DRAWINGS

In the drawings, in which like reference numerals and letters indicate corresponding parts throughout the several views:

FIG. 1 is a view taken of a preferred embodiment of the present invention in a locked or erect position. A cutaway reveals a dumbbell connector.

FIG. 2 is a view of a preferred embodiment of the present invention in an unlocked or non-axially aligned position. A cutaway reveals the spring plunger pressing against a dumbbell connector. Dotted lines show the present invention in the locked position and in a position where both sides of the dumbbell connector are unlocked.

FIG. 3 is a cutaway showing a spring plunger in a female segment pressing a rider against the flat surface of a connector.

FIG. 4 is a cutaway showing a dumbbell connector fully locked by the action of two spring plungers pressing riders against flat surfaces of the connector.

FIG. 5 is a cutaway showing the position of the spring plunger and rider when the connector is in the unlocked position. Dotted lines show the locked position and another rotation of the unlocked position.

DETAILED DESCRIPTION OF THE PREFERRED EMBODIMENT

Referring now to the drawings, a preferred embodiment of a mechanical penile prosthesis in accordance with the principles of the present invention is illustrated in FIGS. 1 and 2, the penile prosthesis generally referred to by the reference numeral 20. The prosthesis 20 is generally shown as an elongated member including a proximal end portion 22 and a distal end portion 24.

The prosthesis 20 of the present invention is designed for implantation one in each of the corpora cavernosa of the penis by standard surgical procedures for treatment of erectile impotence. The prosthesis 20 is configured to generally match penile corpora cavernosa size so as to extend sufficiently proximally and distally when anchored within the penis and body cavity so as to induce an erected penile state generating sufficient stiffness of the penis for intercourse when locked and to provide the penis with flaccid characteristics when unlocked.

The proximal end portion 22 and the distal end portion 24 are either joined directly together, or joined indirectly by one or more connectors or double female or male-female middle segments, and or one or more segments. The segments might be attached in any of several ways, such as by a dumbbell connector 21 mating in the ball sockets 30 of female ends of adjacent segments. Another method of attachment is by a male segment which has a truncated arm 23 (FIG. 3) mating with an adjacent female segment which has a ball socket 30 to receive the male segment.

The female end of a segment contains a locking mechanism for either a flat surfaced spherical arm 23 or a dumbbell connector 21. A preferred locking mechanism can be seen in FIGS. 2, 3, 4, and 5. An axially aligned spring 27 located in a blind hole extending inwardly from the ball socket 30 presses a flat rider 29 against the flat surface or the connector. The force of this spring plunger locks the segments into an axially aligned erect position as seen in FIGS. 1, 3, and 4.

In use, the implanted prosthesis 20 is normally maintained in an unlocked, non-axially aligned position which does not interfere with bending or moving of the penis. An erection is produced simply by elevating the otherwise flaccid penis containing the surgical implant, to the erect position. Manual elevation of the penis causes the dumbbell shaped connectors 21, or the truncated spherical arm 23 of an adjacent segment to rotate in the ball socket 30 until the adjacent segments are axially aligned. The alignment of the segments causes a rider 29 to press against the flat surface of either a dumbbell shaped connection 21 or the flat surface of the truncated spherical arm 23, and the hinge self-locks. Each set of adjacent segments operate independently of all other segments, and each side of the dumbbell shaped connector 21 can be individually rotated into the locked or erect position.

Subsequent restoration of the penis to its dependent state is achieved by again bending the prosthesis 20 into a curved shape. The force in bending is increased gradually to a point where the dumbbell connector 21 or the truncated spherical arm 23 rotates out of the locked position (FIGS. 1, 3, 4) into the normal unlocked position (FIGS. 2, 5). Each locked pair of adjacent segments unlock independent of the others.

Subsequent bending and unbending may be carried out for numerous repetitions with the penis containing the prosthesis 20 being alternately rigid and dependent. The prosthesis 20 thus is bi-stable, it maintains either state until being manually changed.

A preferred embodiment of the prosthesis 20 includes a sheath 28 surrounding the segments and the connectors. A lubricant positioned inside the sheath 28 will insure the long life of the prosthesis although it may be determined that a lubricant is not necessary.

Thus, the penis with the prosthesis of this invention will remain in an increased length and girth condition at all times. It will bend over its entire length but will spring back when released. It will only bend to the dependent position and maintain that position at the hinge area.

It is to be understood, however, even though numerous advantages and characteristics of the invention have been set forth in the foregoing description, together with details of the structure and function of the invention, the disclosure is illustrative only, changes may be made in detail, especially in matters of shape, size and arrangement of parts within the principles of the present invention, to the full extent indicated by the broad general meaning of the terms in which appended claims are expressed.

What is claimed is:

1. A penile erection prosthesis to be fully implanted in a patient having two relatively rigid cylindrically-shaped end segments at least one of the segments having a female end containing a locking mechanism for a flat surfaced connector which joins said segments in two distinct positions, said locking mechanism comprising an axially aligned biasing means located in a receiving means which extends inwardly from a ball socket of said female end, said connector comprising at least one a truncated spherical arm which mates with said ball socket and is secured for rotation within said socket, a first self-locking erect position in which said segments are axially joined and aligned wherein said connected locks into said erect position through the action of the biasing means poressing a flat rider against the flat surface of the spherical arm, and a second unlocked, dependent position in which said segments are joined and non-axially aligned.

2. A penile erection prosthesis according to claim 1 in which said biasing means includes a spring positioned in a blind hole which is located rearward of the ball socket of said female end, said spring being axially aligned with said rider and provides a biasing force thereon.

3. A penile erection prothesis according to claim 2 wherein each of said end segments having said female ends and said connector being dumbbell shaped having two opposing truncated spherical arms each mating with respective said female ends.

4. A penile erection prosthesis according to claim 1 further comprising at least one middle segment disposed between said end segments wherein said middle segment has two opposing female ends each containing said locking mechanisms to operatively mate with said flat surface connector in two said portions.

5. A penile erection prosthesis according to claim 1 in which said flat surface comprising two opposing male ends having opposing said truncated spherical arm which mates with said female end in two said positions.

6. A penile erection prosthesis to be fully implanted in a patient having two relatively rigid cylindrically-shaped end segments, a first end segment having a female end containing a locking mechanism for a flat surface connector, said locking mechanism comprising an axially aligned biasing means located in a receiving means which extends inwardly from a ball socket of said female end, said connector comprising a truncated spherical arm which mates with said ball socket and is secured for rotation within said socket, a second end segment having a male end containing said flat surfaced connector which joins said segment in two positions, a first self-locking erect position in which said segments are joined and aligned wherein said connector locks into said erect position through the action of the biasing means pressing a flat rider against the flat surface of the spherical arm, and a second unlocked position in which said segments are joined and non-axially aligned.

7. A penile erection prosthesis according to claim 6 in which said biasing means includes a spring positioned in a blind hole which is located rearward of the ball socket of said female end of said first end segment, said spring being axially aligned with said rider and provides a biasing force thereon, and positioned in said ball socket of said female end is said first surfaced connector of said male end of said second end segment which has a truncated spherical arm which mates with said ball socket and is secured for rotation within said socket.

8. A penile erection prosthesis according to claim 6 further comprising at least one middle segment having opposing male end and female end which mates with respective said female end and male end of adjacent segments.

9. A penile erection prosthesis according to claims 1, 3, 4, 5, 6 or 8 further comprising a sheath surrounding said segments and said connectors.

10. A penile erection prosthesis according to claim 9 in which said sheath is a silicone tube.

11. A penile erection prosthesis according to claim 9 further comprising a lubricant positioned inside the sheath.

12. A penile erection prosthesis according to claim 11 in which said lubricant is silicone gel.

* * * * *